(12) United States Patent
Raul et al.

(10) Patent No.: US 11,869,643 B2
(45) Date of Patent: *Jan. 9, 2024

(54) GATEWAY CONFORMANCE VALIDATION

(71) Applicant: Apple Inc., Cupertino, CA (US)

(72) Inventors: Meghan Tushar Raul, Sunnyvale, CA (US); Sangeeth Sridharan, San Jose, CA (US); Jorge Fernando Pozas Trevino, San Mateo, CA (US); Pablo Antonio Gonzalez Cervantes, Cupertino, CA (US); Mohan Singh Randhava, San Carlos, CA (US); Sean Robert Moore, San Francisco, CA (US); Todd D. Power, San Carlos, CA (US); Dongsheng Zhang, Santa Clara, CA (US); Eric K. Kimn, Cupertino, CA (US); Pascal B. Pfiffner, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/099,781

(22) Filed: Jan. 20, 2023

(65) Prior Publication Data

US 2023/0154581 A1 May 18, 2023

Related U.S. Application Data

(63) Continuation of application No. 16/443,677, filed on Jun. 17, 2019, now Pat. No. 11,581,072.

(51) Int. Cl.
*G06F 11/30* (2006.01)
*G06F 11/34* (2006.01)
*G16H 10/60* (2018.01)

(52) U.S. Cl.
CPC ........ *G16H 10/60* (2018.01); *G06F 11/3006* (2013.01); *G06F 11/3409* (2013.01)

(58) Field of Classification Search
CPC . G16H 10/60; G06F 11/3006; G06F 11/3409; H04L 67/303; H04L 67/1097; H04L 63/10

(Continued)

(56) References Cited

U.S. PATENT DOCUMENTS 10,586,617 B1 3/2020 McNair
2004/0128369 A1 7/2004 Moreau et al.

(Continued)

OTHER PUBLICATIONS

Non-Final Office Action dated Mar. 24, 2022 in U.S. Appl. No. 16/443,677, filed Jun. 17, 2019. 19 pages.

(Continued)

*Primary Examiner* — Chun Kuan Lee
(74) *Attorney, Agent, or Firm* — Kilpatrick Townsend & Stockton LLP

(57) ABSTRACT

A schema is generated to establish a connection between user devices and one or more patient record servers. Generating a schema can include receiving configuration information associated with a patient record gateway, wherein the patient record gateway is associated with one or more patient record servers configured for storing electronic health records for a plurality of patients. Generating a schema can include defining, based at least in part on the configuration information, a schema configured to enable user devices to retrieve, via the patient record gateway, electronic health records from the one or more patient record servers. A schema can be requested by a user device. The schema can be sent to a user device to establish a connection with the one or more patient record servers.

20 Claims, 9 Drawing Sheets

(58) Field of Classification Search
USPC .......................................................... 712/227
See application file for complete search history.

(56) References Cited

U.S. PATENT DOCUMENTS

| | | | |
|---|---|---|---|
| 2015/0156266 A1* | 6/2015 | Gupta | ..................... H04L 67/12 |
| | | | 709/224 |
| 2017/0134884 A1* | 5/2017 | Taborn | ................... H04W 76/14 |
| 2019/0379725 A1* | 12/2019 | Wada | ...................... H04L 67/12 |
| 2021/0105233 A1 | 4/2021 | Tran et al. | |

OTHER PUBLICATIONS

Notice of Allowance dated Oct. 17, 2022 in U.S. Appl. No. 16/443,677, filed Jun. 17, 2019. 11 pages.

* cited by examiner

GATEWAY CONFORMANCE VALIDATION

CROSS-REFERENCE TO RELATED APPLICATIONS

This application is a continuation application of U.S. patent application Ser. No. 16/443,677 entitled "GATEWAY CONFORMANCE VALIDATION," filed on Jun. 17, 2019, which is herein incorporated by reference in its entirety for all purposes.

BACKGROUND

Users typically visit more than one health institution (e.g., medical providers) to obtain medical treatment. For example, a user may periodically visit a neighborhood clinic for annual physical evaluations and for minor medical procedures. An electronic health record (EHR) is a computer-stored and transferrable copy of a user's physical health record. The neighborhood clinic may maintain an instance of the user's electronic health record (e.g., using an EHR system, sometimes referred to as an electronic medical record (EMR) system). When the user visits a provider, a medical professional may update the electronic health record. However, different instances of the user's electronic health record may be maintained by other health institutions that are unaffiliated with the neighborhood clinic, which may use different versions of the same EHR system or may even use completely different EHR systems (e.g., developed by a competing company). Thus, instances of the user's health record may be distributed among multiple health institutions, and depending on which type and version of EHR systems used by the health institutions, their records may be stored using multiple different EHR types and versions.

A health record sharing system can include functionality for patients to download these disparate instances of their health records to their user devices. For a health institution to have its records available on the health record sharing system, the health institution may be required to participate in an onboarding process defined by an operator of the health record sharing system. During the onboarding process, an administrator or other user of the health institution inputs information that describes many technical aspects of the health institution's EHR system. Existing onboarding processes can be time-consuming and error prone.

BRIEF SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer system, including: a first user interface configured to receive a gateway identifier corresponding to a patient record gateway, the patient record gateway associated with one or more patient record servers configured for storing electronic health records for a plurality of patients, and a memory including computer-executable instructions that, when executed by a processor, cause the processor to access a gateway conformance statement based at least in part on identifying information associated with the patient record gateway, the gateway conformance statement defining characteristics and capabilities of the one or more patient record servers. The processor also performs a configuration test of one or more capabilities of the patient record gateway using the gateway conformance statement and a set of test patient credentials. The processor also, in accordance with a determination that the patient record gateway passes the configuration test, adds the patient record gateway to a list of supported patient record gateways. The computer system also includes a second user interface configured to present the list of supported patient record gateways. Other embodiments of this aspect include corresponding computer methods, apparatus, and computer programs recorded on one or more computer storage devices, each configured to perform the actions described herein.

Implementations may include one or more of the following features. The computer system where performing the configuration test of the one or more capabilities includes: validating the one more capabilities. The computer system may also include validating one or more characteristic of the patient record gateway. The computer system where the memory includes additional computer-executable instructions that, when executed by the processor, further cause the processor to at least: parse the gateway conformance statement based at least in part on results of the configuration test. The processor may further define a gateway schema for the patient record gateway based at least in part on parsing the gateway conformance statement. The computer system where the gateway schema defines a protocol for authorization of a patient and retrieval, by the patient using a user device, of a portion of an electronic health record of the patient that is hosted by the patient record gateway. The computer system where accessing the gateway conformance statement includes requesting the gateway conformance statement from the patient record gateway and receiving the gateway conformance statement from the patient record gateway. The computer system where the patient record gateway includes a test version of the patient record gateway that operates in a test environment. The computer system where adding the patient record gateway to the list of supported patient record gateways includes, in accordance with the determination that the test version of the patient record gateway passes the configuration test, adding a production version of the patient record gateway to the list of supported patient record gateways. Implementations of the described techniques may include hardware, a method or process, or computer software on a computer-accessible medium.

One general aspect includes a computer-implemented method, including: receiving a gateway identifier corresponding to a patient record gateway, the patient record gateway associated with one or more patient record servers configured for storing electronic health records for a plurality of patients. The computer-implemented method also includes accessing a gateway conformance statement based at least in part on identifying information associated with the patient record gateway, the gateway conformance statement defining characteristics and capabilities of the one or more patient record servers. The computer-implemented method also includes performing a configuration test of a plurality of capabilities of the patient record gateway using the gateway conformance statement and a set of test patient credentials. The computer-implemented method also includes in accordance with a determination that the patient record gateway passes the configuration test, adding the patient record gateway to a list of supported patient record gateways. Other embodiments of this aspect include corresponding computer systems, apparatus, and computer programs recorded on one or more computer storage devices, each configured to perform the actions of the methods.

Implementations may include one or more of the following features. The computer-implemented method where performing the configuration test of the plurality of capabilities includes instructing a test harness to perform the configuration test by simulating authorization of a test patient using the set of test patient credentials and simulating retrieval of a test electronic health record associated with the set of test patient credentials. The computer-implemented method further including providing a user interface for presentation at a user device, the user interface including the list of supported patient record gateways. The computer-implemented method where the patient record gateway is one of a plurality of patient record gateways provided by a patient record vendor, each patient record gateway of the plurality of patient record gateways associated with a particular gateway conformance statement. The computer-implemented method where the one or more patient record servers are further configured for outputting electronic health record information in accordance with one or more predefined standards. The computer-implemented method where the one or more predefined standards includes the Fast Healthcare Interoperability Resources (FHIR®) standard. The computer-implemented method where the characteristics of the gateway conformance statement (also called capability statement) include an authorization uniform resource locator (URL), a token URL, a resource URL, a first list of supported resources, a second list of supported search parameters, and types of supported interaction. The computer-implemented method where performing the configuration test includes: verifying connectivity of the one or more patient record servers of the patient record gateway using the gateway conformance statement. The computer-implemented method may also include verifying conformance of the patient record gateway with one or more predefined standards for patient record storage and transmission based at least in part on the gateway conformance statement. The computer-implemented method may also include simulating authorization of a user device by the patient record gateway based at least in part on test patient credentials. The computer-implemented method where performing the configuration test includes: identifying one or more resources associated with the patient record gateway based at least in part on the gateway conformance statement, the one or more resources being available at the one or more patient record servers of the patient record gateway. The computer-implemented method may also include parsing the gateway conformance statement to create one or more gateway schemas for accessing patient record data from the one or more resources. The computer-implemented method where performing the configuration test further includes: accessing the one or more resources to obtain test patient record data in accordance with the one or more gateway schemas. The computer-implemented method may also include comparing the test patient data obtained from the one or more resources with a user data standard specification for patient record storage on a user device. Implementations of the described techniques may include hardware, a method or process, or computer software on a computer-accessible medium.

One general aspect includes one or more computer-readable media including computer-executable instructions that, when executed by one or more computer systems, cause the one or more computer systems to perform operations, including: performing a configuration test of a patient record gateway by at least verifying connectivity of one or more patient record servers of the patient record gateway based at least in part on a gateway conformance statement, the gateway conformance statement defining characteristics and capabilities of the one or more patient record servers. The operations also include verifying conformance of the patient record gateway with one or more global standards for patient record storage and transmission based at least in part on the gateway conformance statement. The operations also include identifying one or more resources associated with the patient record gateway based at least in part on the gateway conformance statement, the one or resources being available at the one or more patient record servers of the patient record gateway. The operations also include parsing the gateway conformance statement to create one or more gateway schemas for accessing patient record data from the one or more patient record servers. The operations also include generating a notification including a result of the configuration test. Other embodiments of this aspect include corresponding computer systems, apparatus, and methods, each configured to perform the actions described herein.

Implementations may include one or more of the following features. The one or more computer-readable media where performing the configuration test further includes: accessing the one or more patient record servers to obtain test patient record data in accordance with the one or more gateway schemas. The operations also include comparing the test patient data obtained from the one or more patient record servers with a user data standard specification for patient record storage on a user device. The one or more computer-readable media where performing the configuration test further includes simulating authorization of a user device by the patient record gateway based at least in part on a set of test patient credentials. Implementations of the described techniques may include hardware, a method or process, or computer software on a computer-accessible medium.

DETAILED DESCRIPTION

Figure 1:
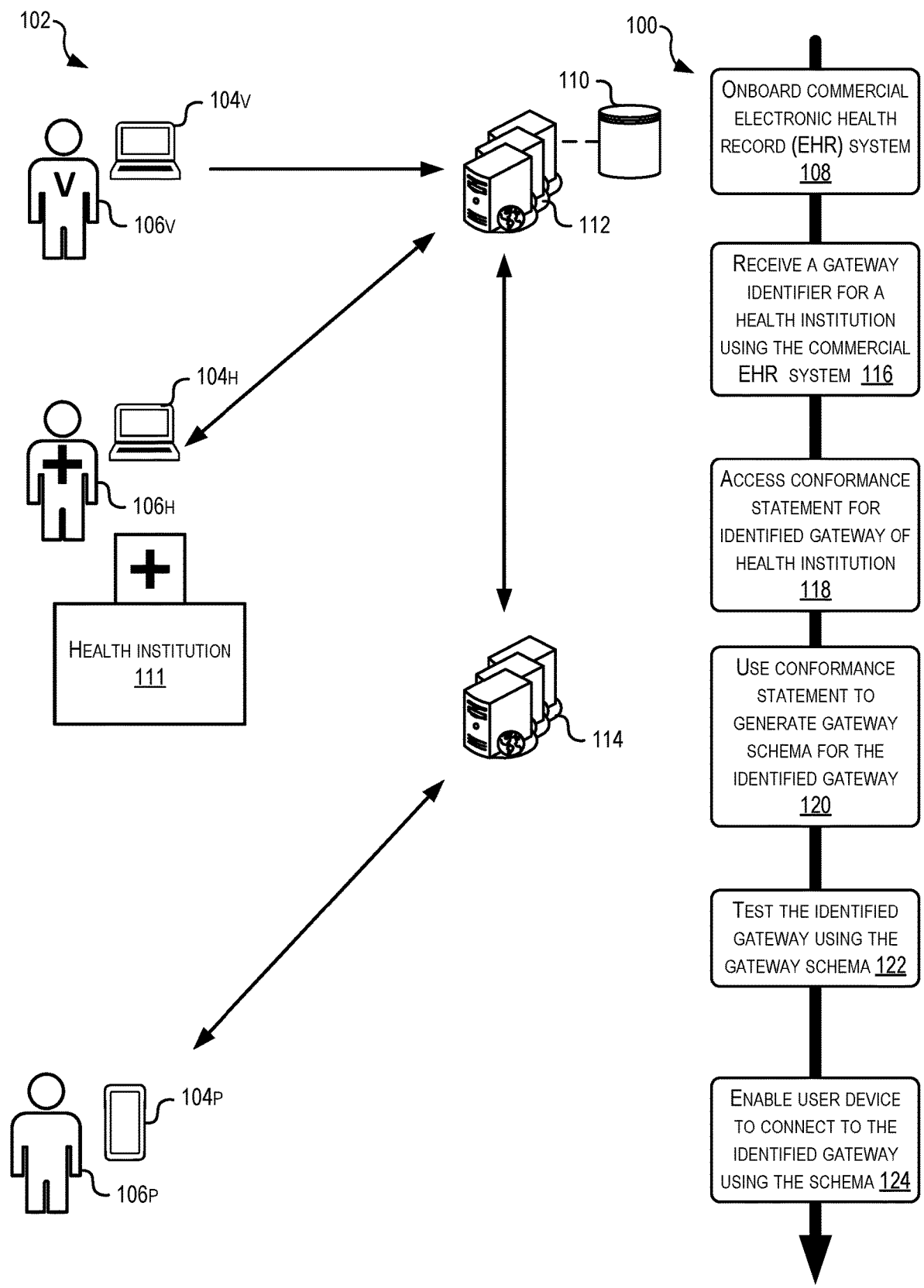
FIG. 1 illustrates a block diagram and a flowchart for onboarding a health institution to a provider cloud using a conformance statement, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, methods, systems, devices, and computer-readable media for efficiently and effectively onboarding health institutions to a provider cloud. In particular, instead of requiring every health institution to arduously provide technical information about its EHR system, the techniques described herein rely on technical information previously gathered from commercial EHR vendors to onboard health institutions. This approach is based on the fact that most health institutions use one or more commercial EHR vendor products and, for the most part, the form of the technical configuration data for each vendor's EHR product will be the same irrespective of the health institution that is being onboarded. Thus, the health institution need only supply information about its gateway (e.g., type and version of EHR system) and the system described herein is able to access the relevant configuration data (e.g., in the form of a conformance statement), perform configuration tests, and perfect the onboarding process with little to no additional burden on the health institution administrators.

The provider cloud allows users to search for relevant health institutions and download, to their smartphones or other user devices, their respective electronic health records from the health institutions. In some examples, this connection may represent a data pipeline connection with the health institution. The provider cloud operates as an intermediary between user devices and gateways of the EHR systems. The gateways are effectively outlets or endpoints provided by the EHR systems. These endpoints are accessible for downloading data from the EHR systems. The techniques described herein efficiently onboard the gateways, test the gateways, and ensure that quality data connections are possible with the gateways.

The EHR systems may be configured differently from one another. For example, data storage formats, user and administrator functionality, and coding schemas may be unique to each. A purpose of the provider cloud described herein is to enable individual, ongoing data pipelines to be established with each of these disparate sources. Once a pipeline is connected, the provider cloud provides a platform for normalizing the data storage formats, user and administrator functionality, and coding schemas from these disparate sources. Thus, once each pipeline has been connected, the data may be stored on a user device in a uniform format, with a predefined set of user functionality, and according to a single coding schema. Doing so results in not only a technical improvement to a computing device, but does so in a way that stores data from the disparate sources in an optimized manner. The data is optimized as to storage capacity and storage access. Because of this, the computing device operates more efficiently than other devices that access electronic health records. This effectively frees up other computing resources for performing other processes.

Generally, the provider cloud enables a process for onboarding new health institutions such that user devices can establish connections to their EHR systems. The gateways share electronic health records with the user devices using an industry standard format such as Fast Healthcare Interoperability Resources (FHIR®) created by the Health Level Seven (HL7®) International standards organization.

Turning now to the figures, FIG. 1 illustrates a block diagram 102 and a flowchart showing a process 100 for onboarding a health institution to a provider cloud using a conformance statement, according to at least one example. The diagram 102 includes patient user device 104p, which can be any suitable electronic user device capable of communicating with other electronic devices or systems over a network such as the Internet. In some examples, the user device 104p can be a smartphone or other user device on which specialized applications can operate. The user device 104p is associated with or otherwise operated by a user 106p. The user 106p is an example of a patient whose electronic health records are the subject of this specification.

The diagram 102 also includes a vendor user device 104v. The vendor user device 104v can be any suitable electronic user device capable of communicating with other electronic devices or systems over a network such as the Internet. In some examples, the vendor user device 104v can be a laptop, personal computer, or other user device on which a vendor user 106v may interact. The vendor user 106v is an example of a representative of a commercial EHR vendor (e.g., an administrator). Examples of commercial EHR vendors include companies such as Cerner, Epic, Meditech, and other such companies that provide applications for storing health records and, in some examples, operating a health institution. The vendor user 106v uses the vendor user device 104v to interact with a provider cloud 112. The provider cloud 112 is used to onboard and manage which entities such as health institutions, EHR systems, and other such entities can be accessed for downloading EHR data for patients. For example, the provider cloud 112 onboards different types and versions of EHR products so that configuration details for the EHR products are made available by the provider cloud 112. The provider cloud 112 also functions to enable users such as the patient user 106p to subscribe to particular entities to create pipelines for downloading EHR data for the patient user 106p.

The diagram 102 also includes a health institution user 106h who uses the health institution user device 104h to interact with the provider cloud 112. For example, the health institution user 106h may use the health institution user device 104h to subscribe the health an EHR system of the health institution to the provider cloud 112.

Medical information associated with the health institution (e.g., electronic health records of patients of the health institution) is stored at one or more EHR system(s) 114. The EHR system 114 may be associated with one or more health institutions (e.g., organization entities, brand entities, and/or location entities). In particular, the EHR system 114 may store, organize, and/or otherwise manage health record data generated by medical professionals of the health institutions. The EHR system 114 includes one or more gateways, each including one or more endpoints to enable multiple connections between the EHR system 114 and other electronic devices. In some examples, user devices such as the patient user device 104p may interact with the EHR system 114 using any suitable interfaces such as gateway application programming interfaces (API). The gateway APIs may define a set of function calls for communications between the EHR system 114 and the user device 104p.

Figure 9:
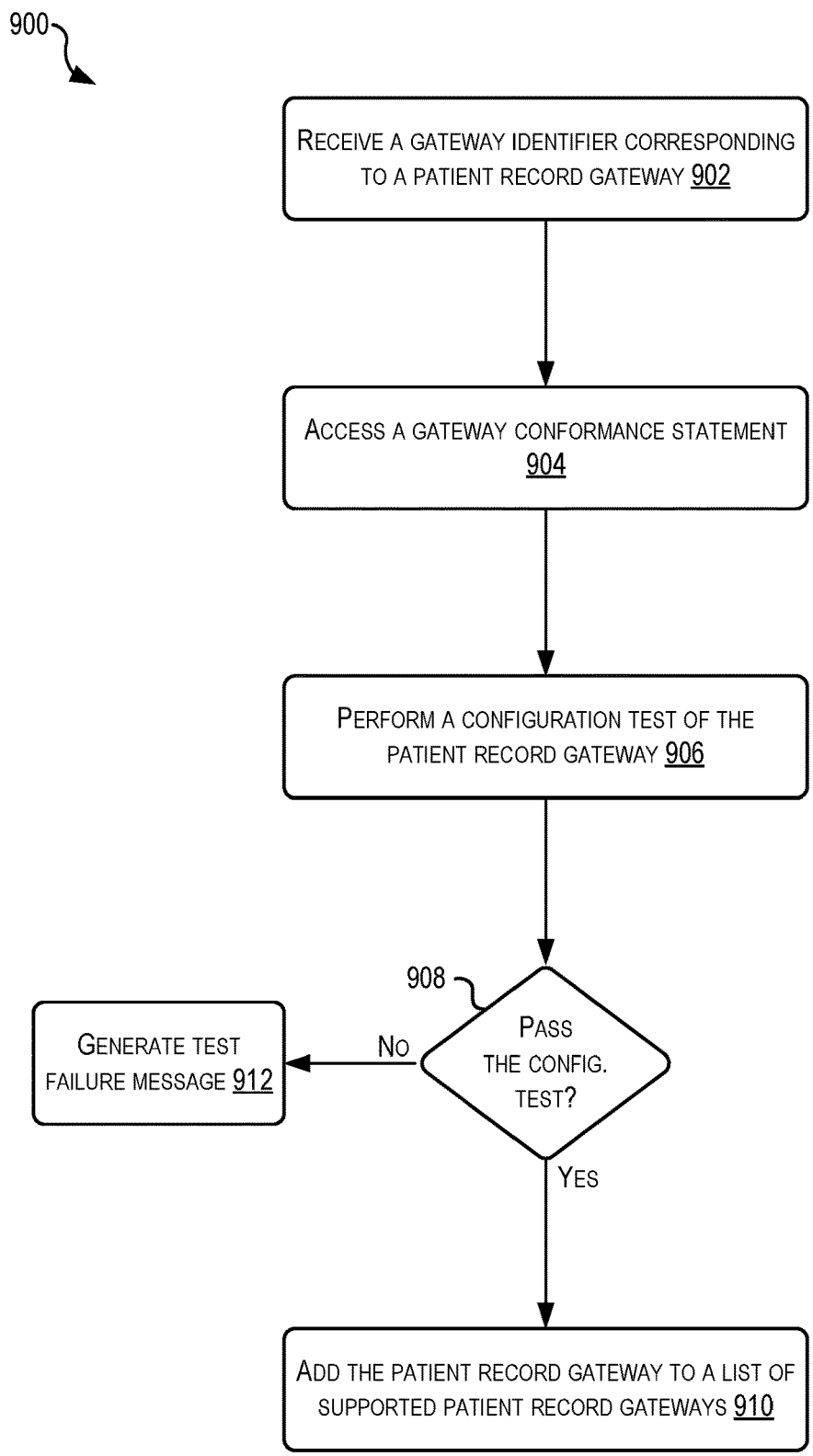
FIG. 9 illustrates an example flow chart showing a process for onboarding a health institution to a provider cloud using a conformance statement, according to at least one example.

FIGS. 1 and 9 illustrate example flow diagrams showing processes 100 and 900, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

The process 100 begins at 108 by onboarding a commercial EHR. The provider cloud 112 performs 108 based on information received from the vendor user device 104v. For example, the vendor user 106v may use the vendor user device 104v to provider configuration data (e.g., authentication, tokens, resources addresses) to the provider cloud 112 responsive to a set of prompts generated by the provider cloud 112. In some examples, the set of prompts are included in a form-fillable webpage provided at the vendor user device 104v. At 108, the vendor user 106v may provide configuration data for each commercial EHR system offered by the commercial vendor. This can include multiple versions of the commercial EHR system, custom builds of the EHR system for certain customers, and the like. In this manner, the provider cloud 112 will include configuration data for multiple commercial EHR systems. The configuration data includes, in some examples, standard addresses for patient record servers, communication protocols used for communicating with the commercial EHR system, authentication protocols, web addresses for particular services, and the like. At 108, the process 100 also includes storing the configuration data for the commercial EHR system within a provider database 110.

At 116, the process 100 includes receiving a gateway identifier for a health institution 111 using the commercial EHR system 114. The provider cloud 112 performs 116. For example, the health institution users 106h may use the health institution user devices 104h to share information about the health institution 111 with the provider cloud 112. The gateway identifier refers to a network address of an endpoint of the EHR system 114 used by the health institution 111. The endpoint is a connection point of the EHR system 114 that enables sharing of patient record data stored by the EHR system 114. The gateway identifier may take any suitable format such as a path, a uniform resource locator (URL), or other such manner for representing the network address. In some examples, the gateway identifier is referred to as a FHIR base URL.

In some examples, the health institution user 106h may easily provider the gateway identifier using a user interface provided by the provider cloud 112. For example, the health institution user 106h may use the health institution user device 104h to navigate to a webpage associated with the provider cloud 112 and there input the gateway identifier. As part of inputting this data, the health institution user 106h may identify the type and version of EHR system 114 used by the health institution 111. For example, the user 106h may designate that the health institution 111 uses "Best EHR Storage" system, version 2.1.3. Based on the gateway identifier and, in some examples, the type and version information, the provider cloud 112 relies on a record in the database 110 created at 108 for continuing the onboarding process for the health institution 111, instead of requesting additional information from the health institution user 106h. In some examples, resolving the gateway identifier enables the provider cloud 112 to determine the type and version of EHR system 114 used by the health institution 111.

At 118, the process 100 includes accessing a conformance statement for the identified gateway of the health institution 111. This is performed by the provider cloud 112. For example, the provider cloud 112 may use the gateway identifier to access the gateway of the EHR system 114 and obtain the conformance statement from the EHR system 114 used by the health institution 111. In some examples, the conformance statement defines a set of capabilities and characteristics of the gateway of the EHR system 114. It may be used as a statement of the actual functionality of the underlying server(s) that make up the EHR system 114 and are available via the gateway. The conformance statement essentially provides the know-how for interacting with the EHR system 114. In this manner, the conformance statement can be used in place of obtaining technical configuration details from the health institution user 106h. In some examples, the conformance statement is an example of a "capability statement" as used in Fast Healthcare Interoperability Resources (FHIR®) STU-3 and later.

At 120, the process 100 includes using the conformance statement to generate a gateway schema for the identified gateway of the health institution 111. This is performed by the provider cloud 112. In some examples, block 122 is conditional on the gateway passing the test at block 120. The schema may include at least a portion of the conformance statement information and other information discovered, generated, or otherwise obtained during the testing at block 120. In particular, generating the schema may include validating the information during testing at block 120 and parsing the conformance statement into the schema that is specific to the gateway of the health institution 111.

At 122, the process 100 includes testing the identified gateway of the health institution 111 using the gateway schema. This is performed by the provider cloud 112. In some examples, the testing involves testing the set of capabilities and confirming the characteristics of the gateway. Testing can include testing against an industry standard specification for sharing health data such as the FHIR standard. Testing can also include testing against one or more other specifications such as one created by an operator of the provider cloud 112. While the FHIR standard may identify general standards for sharing health data, the operator-created standard may define specific standards to ensure a consistent user experience for users who download their medical records from the EHR system 114 (e.g., the patient user 106p).

In some examples, the testing occurs with respect to a testing gateway. In this manner, errors identified during testing can be rectified before production gateway is made available for user connections. The testing can include simulating a user connection to the gateway and downloading a patient health record.

At 124, the process 100 includes enabling a user device to connect to the identified gateway (e.g., the gateway of the EHR system 114) of the health institution 111 using the gateway schema generated at block 122. This is performed by the provider cloud 112. For example, the patient user device 104p may connect to the EHR system 114 using the gateway schema, which may be shared with the patient user device 104p by the provider cloud 112 when the user device 104p first attempts to connect to the gateway of the EHR system 114. Downloading health record data may include downloading electronic health records using the FHIR standard. In some examples, the patient user device 104 may connect to and download from more than one EHR system 114.

Figure 2:
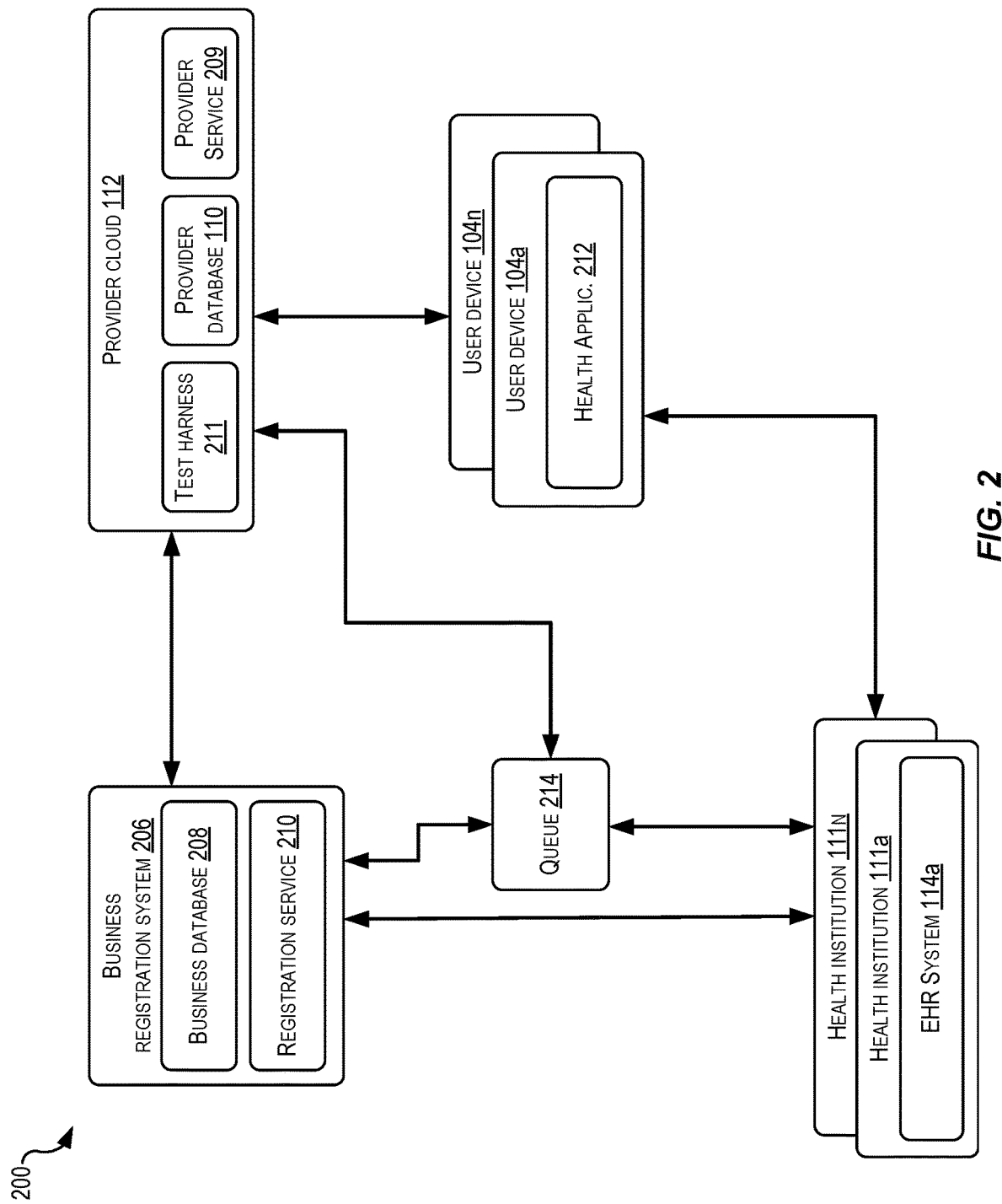
FIG. 2 illustrates a block diagram showing an example architecture or system for onboarding a health institution to a provider cloud using a conformance statement, according to at least one example.

FIG. 2 illustrates a block diagram showing an example architecture or system 200 for onboarding a health institution to a provider cloud using a conformance statement, according to at least one example. The system 200 includes a few elements introduced in FIG. 1. In particular, the system 200 includes the provider cloud 112, one or more user devices 104a-104n, and one or more EHR systems 114a-114n associated with one or more health institutions 111a-111n. The provider cloud 1112 also includes a business registration system 206 and a queue 214. As appropriate and as illustrated by the arrows, the elements of the system 200 may be communicatively coupled via one or more networks.

Beginning with the business registration system 206, the business registration system 206 may be any suitable collection of hardware and software components configured to collect, store, update, and otherwise manage business locations including those of the health institutions 111. For example, the business registration system 206 may include a business database 208 and a registration service 210 to enable subscription of the health institution 111. When health institution 111 is subscribed and active, the user devices 104 may be allowed to connect to and download health record data from the associated EHR system 114 (e.g., a gateway of the EHR system 114).

As part of subscribing and managing subscriptions, the registration service 210 may include functionality to collect, store, update, and otherwise manage business locations. In some examples, the registration service 210 provides one or more user interfaces by which authorized users may input information about their location. This information may include geographic information (e.g., a physical address and pin on a map), image information (e.g., logos), contact information (e.g., business, legal, technical, etc.), and any other information relating to a business. The registration service 210 may also be configured to create and/or update record entries in the business database 208 based on information received. For example, an authorized user associated with the health institution 111 may share business information with the business registration system 206. Once this information has been shared and validated, the business information may be published for public consumption (e.g., indexed for searching, made available on a map platform, shared directly with users, etc.).

The business database 208 may maintain the collected business information and any relationships between entities represented by the business information. In some examples, the business database 208 includes some or all of the information stored in the provider database 110. For example, because the business registration system 206 may be used to register all business (not just health institutions 111), records for the health institutions 111 may be maintained in both the business database 208 and the provider database 110. In some examples, the business registration system 206 shares business information with the provider cloud 112 in any suitable manner.

Turning now to the provider cloud 112, the provider cloud 112 may include the provider database 110 introduced herein, a provider service 209, and a test harness 211. Generally, the provider cloud 112 may validate the EHR systems 114, maintain information about the health institutions 111 and associated EHR systems 114, enable searching of the health institutions 111 associated with the EHR systems 114, and manage access of the user devices 104 to the EHR systems 114.

After a health institution 111 associated with an EHR system 114 has been subscribed, the test harness 211 of the provider cloud 112 may be used to test and/or otherwise validate that the EHR system 114 meets certain standards associated with sharing health data. In some examples, the testing may be based, at least in part, on a conformance statement associated with the EHR system 114.

The testing can include simulating that a test user using a test user device 104 can connect to and download data from the EHR system 114. In this manner, the test harness 211 may simulate actions that one of the user devices 104 may perform to connect to the EHR system 114. In some examples, the test harness 211 may test this connection when a health institution 111 is first subscribed and at other times after the initial subscription. For example, the connection may be tested periodically, when certain conditions are fulfilled, and under any other circumstance. If the test is positive, a status indicator(s) in the provider database 110 associated with the health institution 111, the EHR system 114, and/or a gateway associated with the EHR system 114 may be updated to reflect that the EHR system 114 or the gateway is/are active. If the test is negative, the status indicator(s) may be updated to reflect that the EHR system 114 is inactive. When active, the user devices 104 may be capable of connecting to the gateways of the EHR systems 114. When inactive, the user devices 104 may be unable to connect to the gateways of the EHR systems 114.

The provider service 209 may maintain information about the health institutions 111 and associated EHR systems 114 in the provider database 110, enable searching of the health institutions 111 associated with the EHR systems 114, and manage access of the user devices 104 to the EHR systems 114. In some examples, the user devices 104 send requests to search for the health institutions 111 to the provider service 209. The provider service 209 processes these requests and returns results. In some examples, as part of establishing a connection with one of the EHR systems 114, the user device 104 will check in with the provider service 209 to determine whether any configuration information, which may be saved as a gateway schema, associated with the EHR system 114 has changed. The gateway schema, which may be stored in the provider database 110 may include API information, provider identifiers, status indicator information, and any other suitable information relating to the configuration of the EHR system 114 and/or other entities associated with the EHR system 114.

The user devices 104 may include a health application 212. Generally, the user devices 104 may be associated with and operated by different users (e.g., patients of the health institutions 111, employees of the health institutions 111). Functionally, the health application 212 may enable the user devices 104 to communicate with the provider cloud 112

(e.g., to search for the health institutions 111, obtain configuration information about the health institutions 111, and perform other actions), and communicate with the EHR systems 114 of the health institutions 111 (e.g., to download data packages including electronic health records and/or updates to electronic health records and to perform other such techniques).

The queue 214 is configured to broker messages between the health institutions 111, the provider cloud 112, and the user devices 104. In some examples, the queue 214 receives requests from producer entities and enables delivery to consumer entities. In some examples, the queue 214 is used to receive requests and pass them directly the other entities, to schedule certain actions, and the like. The queue 214 is configured to provide a unified, high-throughput, low-latency platform for handling real-time data feeds. In some examples, a storage layer of the queue 214 may include a scalable pub/sub message queue designed as a distributed transaction log. In some examples, the queue 214 connects to external systems (for data import/export) via a connect application and provides data streaming using a stream processing library. In some examples, the queue 214 is built on the Apache Kafka platform.

Figure 3:
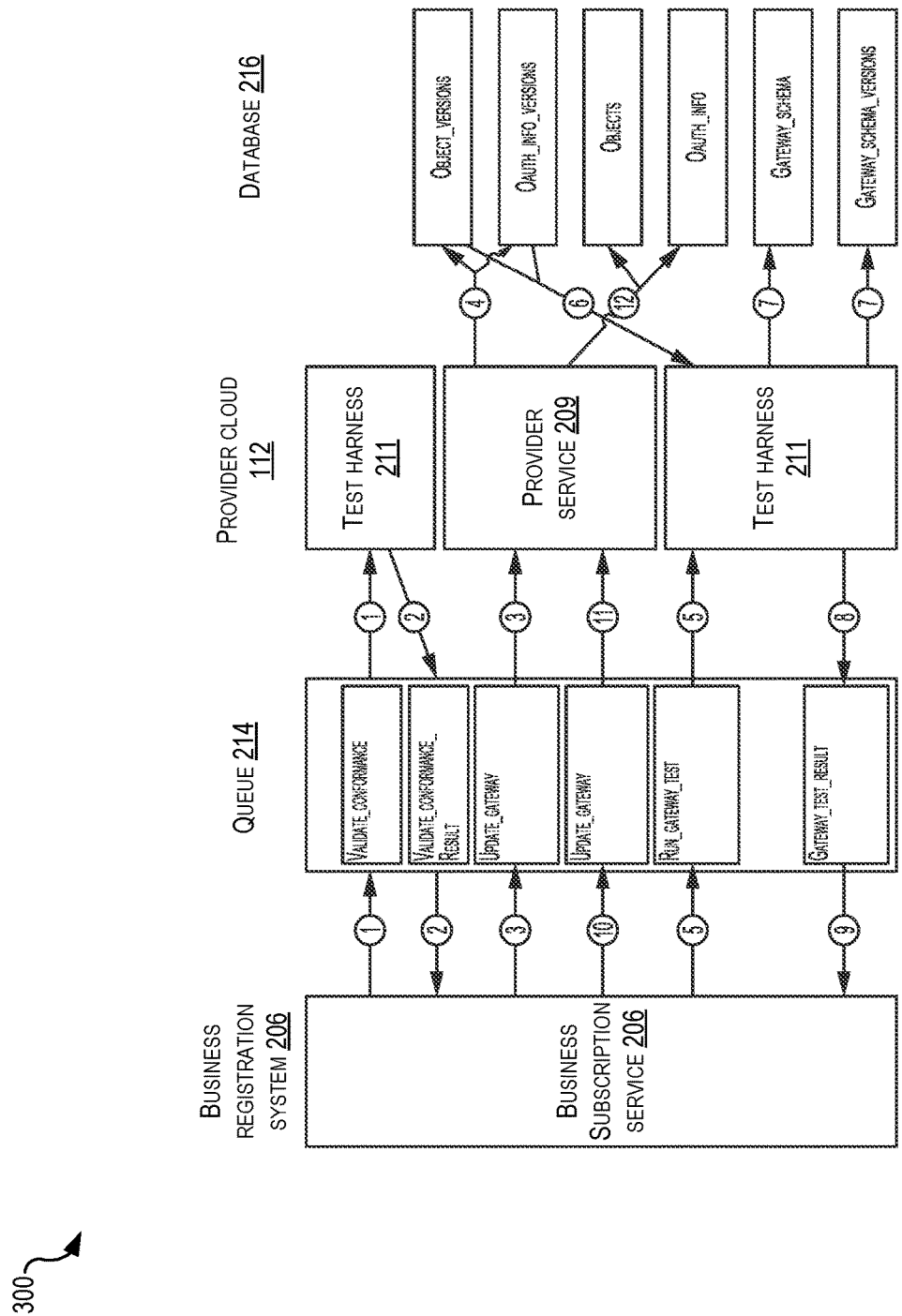
FIG. 3 illustrates a data flow for onboarding a health institution including a custom electronic health record system to a provider cloud using a conformance statement, according to at least one example.

FIG. 3 illustrates a data flow 300 for onboarding a health institution including a custom electronic health record system to a provider cloud using a conformance statement, according to at least one example. The flow 300 is performed by the business registration system 206, the queue 214, the provider cloud 112, and a database 216. The database 216 may include a distributed, wide column store, NoSQL database management system designed to handle large amounts of data across many commodity servers. Such an arrangement may provide high availability with no single point of failure. In some examples, the database 216 provides robust support for clusters spanning multiple datacenters, with asynchronous masterless replication allowing low latency operations for all clients. In some examples, the database 216 is built on the Apache Cassandra platform.

The data flow 300 begins at (1) by the business registration system 206 sending a message to the queue 214 to validate conformance of a conformance statement of a gateway. In some examples, prior to the data flow 300 beginning at (1), the conformance statement is accessed from the gateway of a health institution or provided to the business registration system 206 in some other manner. In any event, at (1) the data flow 300 also includes the test harness 211 validating the conformance statement, which can include validating a gateway identifier for the gateway, validating a gateway version, and validating an address associated with the gateway (e.g., a FHIR-based URL).

At (2), the data flow 300 includes the test harness 211 sharing the results of the conformance test with the queue 214, which are then shared with the business registration system 206.

At (3), the data flow 300 includes the business registration system 206 sending a message to the queue 214 to update the gateway. This can include a message to update a client identifier, a client secret, a scope associated with the conformance statement, a base address for the gateway (e.g., base URL), and a version identifier. Also at (3), the data flow includes the queue 214 sending a message to the provider service 209 to update the gateway the information identified previously. At (3), the status of the gateway may be unpublished, e.g., unavailable, when searched by a user device. In some examples, the testing is performed on a test gateway within a sandbox environment.

Updating the gateway can include, at (4), updating versions of objects for the conformance statement stored in the database 216 and/or updating authorization information versions stored in the database 216. These updating steps may correspond to the client identifier, the client secret, the scope associated with the conformance statement, the base address for the gateway (e.g., base URL), and the version identifier.

At (5), the data flow 300 includes the business registration system 206 sending a message to the queue 214 to run a gateway test. In some examples, the queue 214 passes the message to the test harness 211 of the provider cloud 112 to perform the gateway test. The gateway test can include the test harness 211 performing one or more configuration tests using the conformance statement. For example, the test harness 211 can test links to patient record servers identified in the conformance statement, download test patient data, simulate a user device connection to the provider cloud 112, simulate a download of test patient data from the gateway, and confirm that the downloaded data corresponds to one or more standards.

Testing the gateway can include, at (6) and (7) accessing object version information from the database 216 and testing the gateway schema and the gateway schema versions. These testing steps may correspond to the test harness 211 performing the configuration test described previously.

At (8), the data flow 300 includes sharing the gateway test results with the business registration system 206 via the queue 214, at (9). Once the business registration system 206 has the results, it can again begin the process of updating the gateway, which includes (10), (11), and (12). In some examples, the updating at (10) may include updating at least some of same data elements updated at (3). However, the update at (10) may result in the status of the gateway changing from not published to published. This may make the gateway a production gateway.

Figure 4:
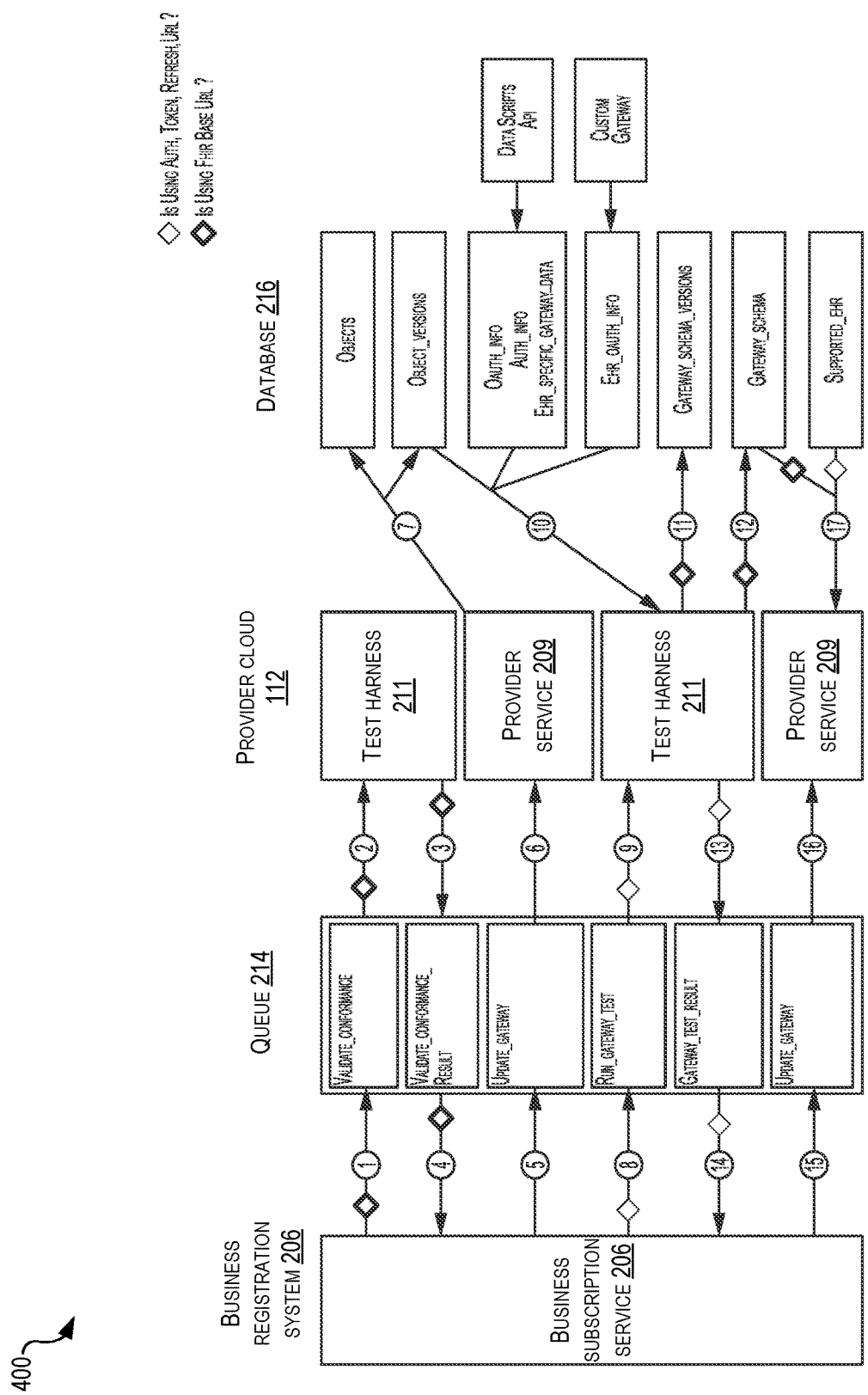
FIG. 4 illustrates a data flow for onboarding a health institution including a commercial electronic health record system to a provider cloud using a conformance statement, according to at least one example.

FIG. 4 illustrates a data flow 400 for onboarding a health institution including a custom electronic health record system to a provider cloud using a conformance statement, according to at least one example. The flow 400 is performed by the business registration system 206, the queue 214, the provider cloud 112, and the database 216.

The data flow 400 begins at (1) by the business registration system 206 sending a message to the queue 214 to validate conformance of a conformance statement of a gateway. In some examples, prior to the data flow 300 beginning at (1), the conformance statement is accessed from the gateway of a health institution or provided to the business registration system 206 in some other manner. In any event, at (2) the data flow 300 also includes the test harness 211 validating the conformance statement, which can include validating a gateway identifier for the gateway, validating a gateway version, and validating an address associated with the gateway (e.g., a FHIR-based URL).

At (3) and (4), the data flow 400 includes the business registration system 206 receiving, via the queue 214, the results of the conformance statement validation performed at (2).

At (5), the data flow 400 includes the business registration system 206 sending message to the queue 214 to update the gateway. This can include a message to update a client identifier, a client secret, a scope associated with the conformance statement, a base address for the gateway (e.g., base URL), and a version identifier. At (6), the data flow 400 includes the queue 214 sending a message to the provider service 209 to update the gateway information identified previously. At (5), the status of the gateway may be unpublished, e.g., unavailable when searched by a user device. In some examples, the testing is performed on a test gateway within a sandbox environment.

Updating the gateway can include, at (7), updating versions of objects for the conformance statement stored in the database 216 and/or updating authorization information versions stored in the database 216. These updating steps may correspond to the client identifier, the client secret, the scope associated with the conformance statement, the base address for the gateway (e.g., base URL), and the version identifier.

At (8), the data flow 400 includes the business registration system 206 sending a message to the queue 214 to run a gateway test. In some examples, this message includes an authorization code. In some examples, at (9), the queue 214 passes the message, which may include the authorization code, to the test harness 211 of the provider cloud 112 to perform the gateway test. The gateway test can include the test harness 211 performing one or more configuration tests using the conformance statement. For example, the test harness 211 can test links to patient record servers identified in the conformance statement, download test patient data, simulate a user device connection to the provider cloud 112, simulate a download of test patient data from the gateway, and confirm that the downloaded data corresponds to one or more standards.

Testing the gateway can include, at (10), accessing object version information, authorization information including testing an application programming interface to a database (e.g., "data scripts API"), and EHR system authorization information including testing a custom gateway from the database 216 and testing the gateway schema versions at (11) and the gateway schema at (12). These testing steps may correspond to the test harness 211 performing the configuration test described previously.

At (13), the data flow 400 includes sharing the gateway test results with the queue 214, which in turns shares the results with the business registration system 206, at (14). Once the business registration system 206 has the results, it can again begin the process of updating the gateway, which includes (15) and (16) using the provider service 209. In some examples, the updating at (15) may include updating at least some of same data elements updated at (6). However, the update at (15) may result in the status of the gateway changing from not published to published. This may make the gateway a production gateway. In some examples, at (17), the data flow 400 includes designating the gateway as a supported EHR system.

Figure 5:
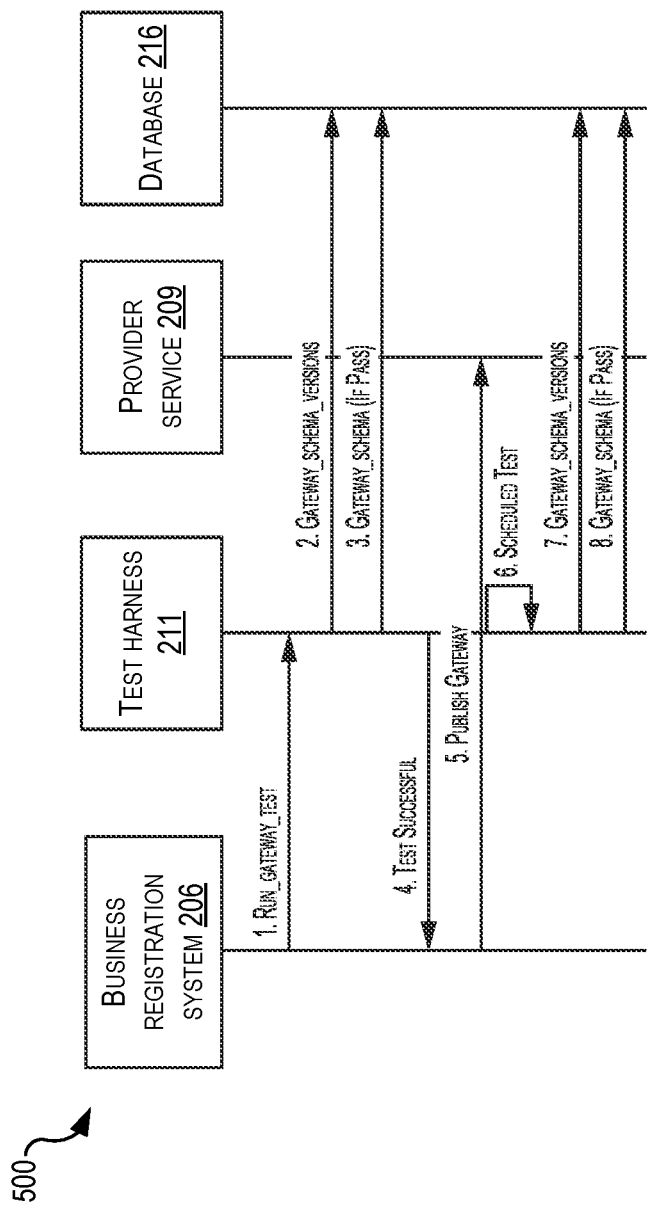
FIG. 5 illustrates a data flow for creating a gateway schema for a gateway of a health institution, according to at least one example.

FIG. 5 illustrates a data flow 500 for creating a gateway schema for gateway of a health institution, according to at least one example. The data flow 500 is performed by the business registration system 206, the queue 214, the provider cloud 112, the database 216.

The data flow 500 begins at (1), by the business registration system 206 requesting the test harness 211 to perform a gateway test. The gateway test can perform as described herein. At (2), the data flow 500 includes the test harness 211 accessing gateway information from the database 216. Such information may include version information for the gateway schema. If the gateway passes the gateway test, then, at (3), the gateway schema is generated. Additionally, at (4), a message is sent to the business registration system 2106 indicating that the test was successful. At (5), the gateway is published to the provider service 209 (e.g., made available within the provider database 110.

Periodic testing of the gateway can be scheduled at (6). Then the testing can be performed at (7) and (8), which correspond to (2) and (3). If the gateway passes again, it will remain available at the provider service 209. If not, the gateway will be removed from a list of supported gateways, as described with reference to FIG. 7.

Figure 6:
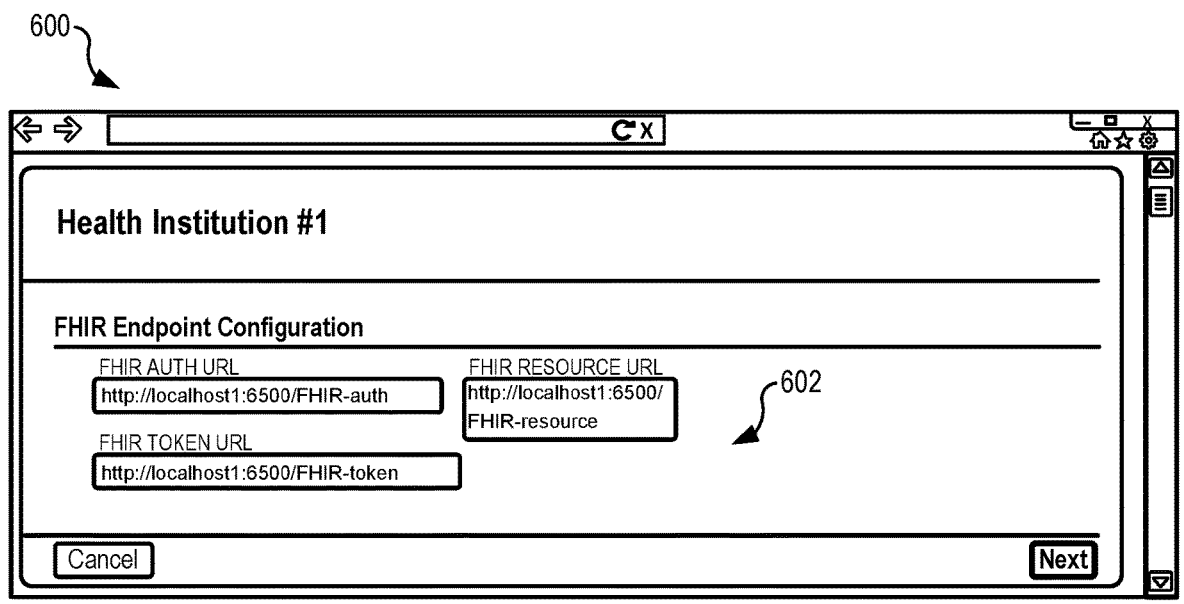
FIG. 6 illustrates a user interface for obtaining configuration data for a gateway of a health institution, according to at least one example.

FIG. 6 illustrates a user interface 600 for obtaining configuration data for a gateway of a health institution, according to at least one example. The user interface 600 can be presented at by the provider cloud 112 at one of the user devices 104 (e.g., a health institution user device 104*h* or a vendor user device 104*v*). The user interface 600 includes an endpoint/gateway configuration area 602. In the endpoint configuration area 602 is presented one or more text input boxes in which can be input configuration data for configuring a gateway. The configuration data includes, for example, an authorization URL, a FHIR resource URL, and a token URL.

Figure 7:
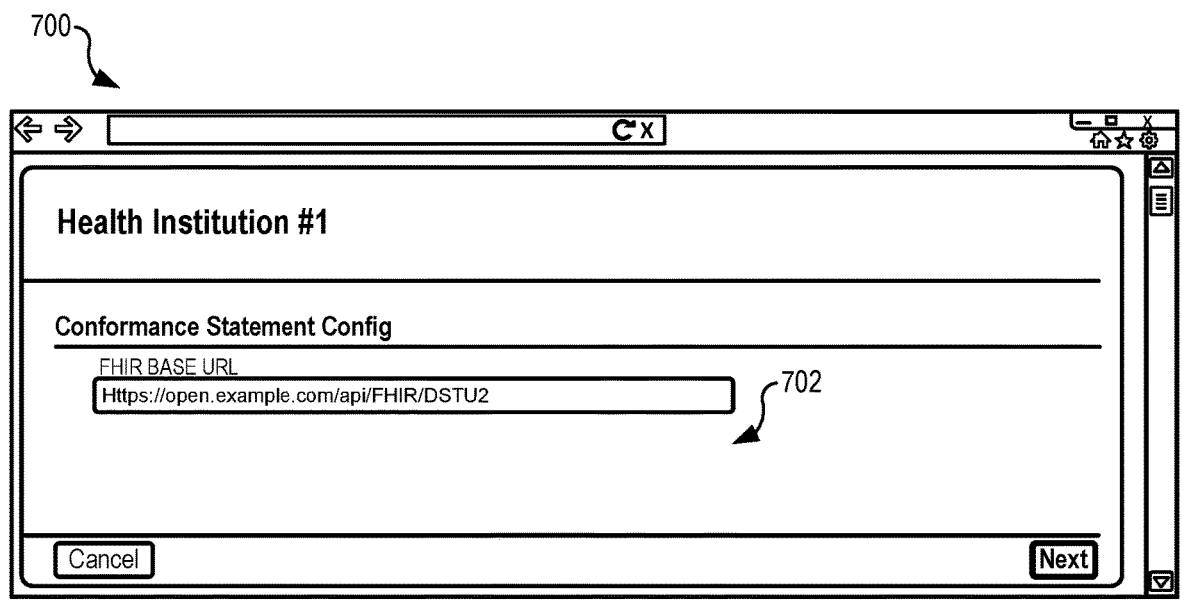
FIG. 7 illustrates a user interface for obtaining configuration data for a gateway of a health institution, according to at least one example.

FIG. 7 illustrates a user interface 700 for obtaining configuration data for a gateway of a health institution, according to at least one example. The user interface 700 can be presented at by the provider cloud 112 at one of the user devices 104 (e.g., a health institution user device 104*h* or a vendor user device 104*v*). The user interface 700 includes an endpoint/gateway configuration area 702. In the endpoint configuration area 702 is presented one or more text input boxes in which can be input data for configuring a gateway. The configuration data includes, for example, a FHIR base URL. The FHIR base URL functions as a gateway identifier. Using the FHIR base URL, the systems described herein can access the conformance statement that includes, among other things, similar configuration data as shown in the endpoint configuration area 602.

Figure 8:
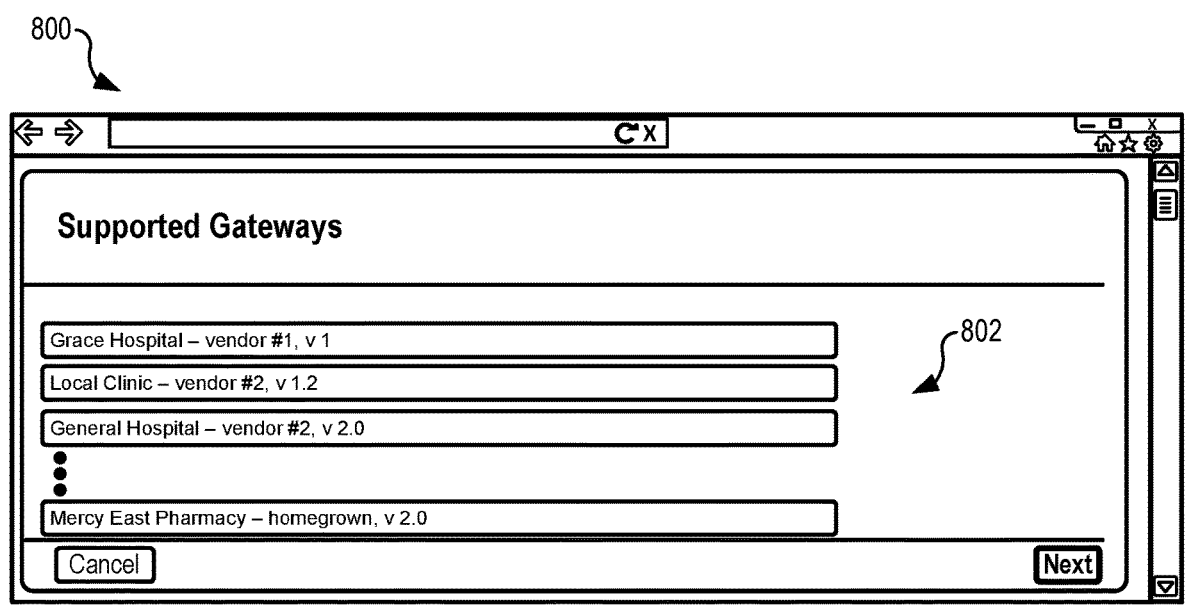
FIG. 8 illustrates a user interface for presenting a list of supported gateways, according to at least one example.

FIG. 8 illustrates a user interface 800 for presenting a list of supported gateways, according to at least one example. The user interface 800 can be presented by the provider cloud 112 at one of the user devices (e.g., the patient user device 104*p*). The user interface 800 includes a supported gateways area 802. In the supported gateways area 802 is presented a list of supported gateways. In some examples, the list of supported gateways may identify the health institution and which EHR system and version are used by each health institution. In some examples, a similar list, but without the health institution name, can be presented at the health institution user device 104*h*. This may be desirable for the health institution user 106*h* to select which EHR system and version the health institution operates. Using this approach may allow the health institution user 106*h* to quickly and efficiently onboard the gateway of their health institution because much of the configuring has already been performed. In particular, the EHR system and versions have been configured, e.g., by the vendor user 106*v*, and the health institution user 106*h* just needs to identify the gateway address and the process can automatically validate the gateway of the health institution as described herein.

FIG. 9 illustrates an example flow chart showing a process 900 for onboarding a health institution to a provider cloud using a conformance statement, according to at least one example. The process 900 begins at 902 by receiving a gateway identifier corresponding to a patient record gateway (e.g., a gateway of an EHR system such as the EHR system 114 (FIG. 1)). This may be performed by the provider service 209 (FIG. 2) of the provider cloud 112 (FIG. 1). In some examples, the gateway identifier is a FHIR base URL associated with the gateway. The gateway identifier may be received via an interface such as the user interface 700 configured to receive the gateway identifier. The patient record gateway may be associated with one or more patient record servers configured for storing electronic health records for a plurality of patients. In some examples, the one or more patient record servers are further configured for outputting electronic health record information in accordance with one or more predefined standards. The one or more predefined standards may include the Fast Healthcare Interoperability Resources (FHIR®) standard. The patient record servers may make up the EHR system 114 described herein. The patient record servers may be hosted by a third-party such as the health institutions or a vendor.

At 904, the process 900 includes accessing a gateway conformance statement. This may be performed by the test harness 211 (FIG. 2) of the provider cloud 112. In some examples, accessing the gateway conformance statement may be based at least in part on identifying information associated with the patient record gateway. For example, the identifying information may be the gateway identifier (e.g., a FHIR base URL) or other identifying information such as an address of a location at the EHR system where the conformance statement is stored other than at the FHIR base URL. The gateway conformance statement may define characteristics and capabilities of the one or more patient record servers.

In some examples, the characteristics of the conformance statement include an authorization Uniform Resource Locator (URL), a token URL, a resource URL, a first list of supported resources, a second list of supported search parameters, and types of supported interaction.

In some examples, accessing the gateway conformance statement may include requesting the gateway conformance statement from the patient record gateway and receiving the gateway conformance statement from the patient record gateway.

At 906, the process 900 includes performing a configuration test of the patient record gateway. This may be performed by the test harness 211 of the provider cloud 112. In some examples, performing the configuration test includes testing a plurality of capabilities of the patient record gateway using the gateway conformance statement and a set of test patient credentials. The test patient credentials may be obtained from the EHR system and/or provided by an administrator of the health institution or vendor that is participating in the onboarding process. The gateway configuration test can include verifying connectivity of one or more patient record servers of the patient record gateway based at least in part on the gateway conformance statement and verifying conformance of the patient record gateway with one or more predefined standards for patient record storage and transmission based at least in part on the gateway conformance statement. The gateway configuration test can also include identifying one or more resources associated with the patient record gateway based at least in part on the gateway conformance statement. The one or resources may be available at the one or more patient record servers of the patient record gateway. The gateway configuration test can also include parsing the gateway conformance statement to create one or more gateway schemas for accessing patient record data from the one or more patient record servers, accessing the one or more patient record servers to obtain test patient record data in accordance with the one or more gateway schemas, comparing the test patient data obtained from the one or more patient record servers with a user data standard specification for patient record storage on a user device, and simulating authorization of a user device by the patient record gateway based at least in part on a set of test patient credentials.

In some examples, performing the configuration test of the plurality of capabilities includes instructing a test harness to perform the configuration test by simulating authorization of a test patient using the set of test patient credentials and simulating retrieval of a test electronic health record associated with the set of test patient credentials.

In some examples, performing the configuration test of the one or more capabilities includes validating the one or more capabilities, and validating one or more characteristic of the patient record gateway. In this example, the process 900 further includes parsing the gateway conformance statement based at least in part on results of the configuration test, and defining a gateway schema for the patient record gateway based at least in part on parsing the gateway conformance statement. The gateway schema may define a protocol for authorization of a patient and retrieval, by the patient using a user device, of a portion of an electronic health record of the patient that is hosted by the patient record gateway.

At 908, the process 900 includes determining whether the patient record gateway passes the configuration test. If the patient record gateway does not pass the configuration test (i.e., the answer at 908 is "No"), the process 900 proceeds to 912, at which a test failure message is generated. This may be performed by the provider service 209 or the test harness 211 of the provider cloud 112. The test failure message may indicate which portions of the test the patient record gateway failed. In some examples, the test failure message may cause the patient record gateway to change states from available to unavailable. For example, when the configuration test is performed after the patient record gateway has been published (e.g., the gateway is a production gateway, not a test gateway), failing the configuration test may cause the product gateway to be disabled. When disabled, the gateway may be unavailable for selection within the list of supported gateways, as described with reference to FIG. 8.

If the patient record gateway passes the configuration test (i.e., the answer at 908 is "Yes"), the process 900 proceeds to 910, at which the patient record gateway is added to a list of supported patient record gateways. This may be performed by the provider service 209 of the provider cloud 112. Adding the patient record gateway may include adding the patient record gateway to the list of supported gateways, as described with reference to FIG. 7.

In some examples, the patient record gateway includes a test version of the patient record gateway that operates in a test environment (e.g., a sandbox). In this example, adding the patient record gateway to the list of supported patient record gateways may include, in accordance with the determination that the test version of the patient record gateway passes the configuration test, adding a production version of the patient record gateway to the list of supported patient record gateways. Passing the configuration test may include achieving positive results on all or a portion of the test criteria.

In some examples, the process 900 further includes providing a user interface for presentation at a user device, the user interface including the list of supported patient record gateways.

In some examples, the patient record gateway is one of a plurality of patient record gateways provided by a patient record vendor. In this example, each patient record gateway of the plurality of patient record gateways is associated with a particular gateway conformance statement.

Figure 10:
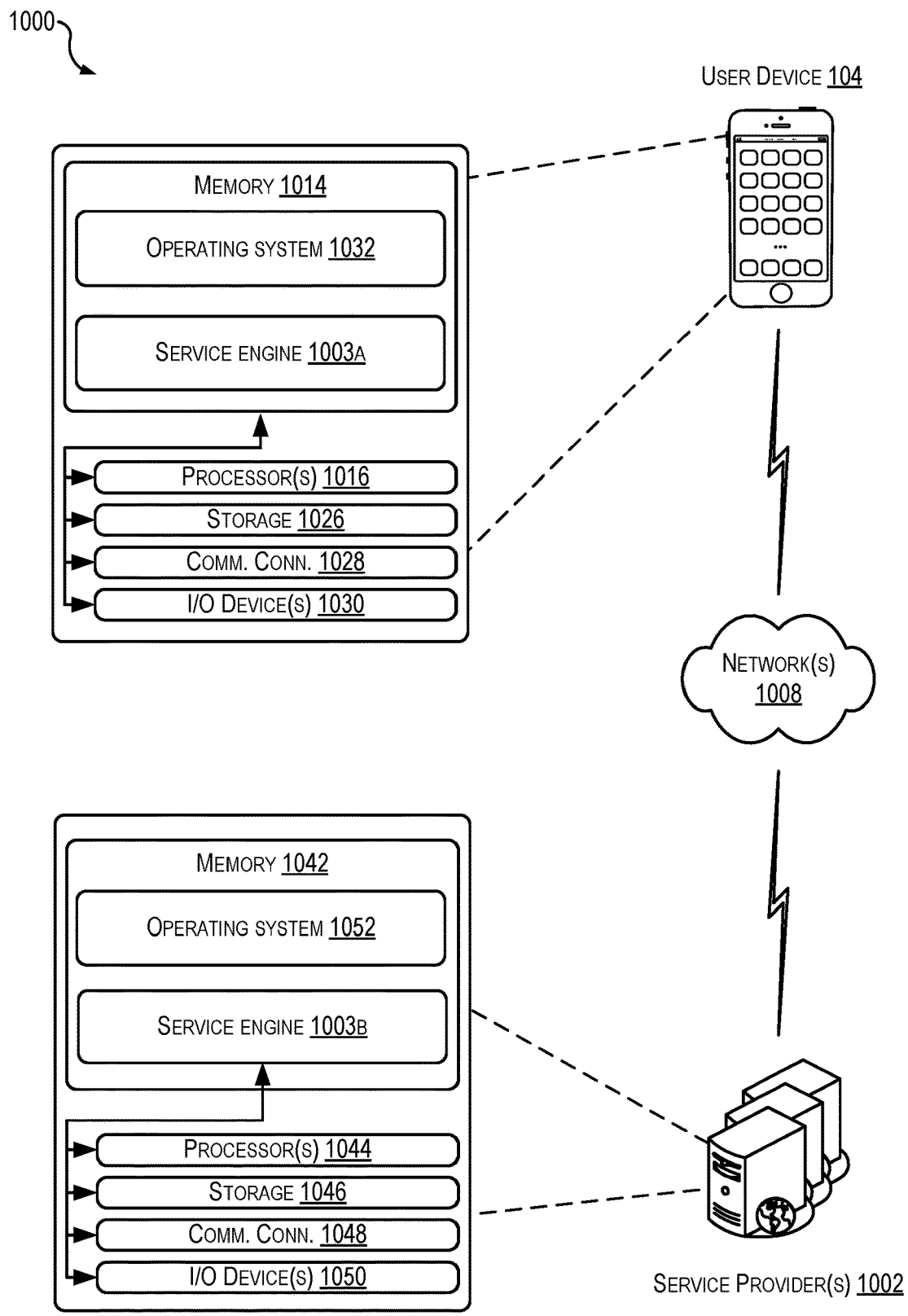
FIG. 10 illustrates a simplified block diagram depicting an example architecture for implementing the techniques described herein, according to at least one example.

FIG. 10 illustrates an example architecture or environment 1000 configured to implement techniques described herein, according to at least one example. In some examples, the example architecture 1000 may further be configured to enable the user device 104, service provider computers 1002 to share information. The service provider computers 1002 are examples of the business registration system 206, the provider cloud 112, and the EHR systems 114. In some examples, the devices may be connected via one or more networks 1008 (e.g., via Bluetooth, WiFi, the Internet, or the like). In some examples, the service provider computers 1002 may be configured to implement at least some of the techniques described herein with reference to the user device 104.

In some examples, the networks 1008 may include any one or a combination of many different types of networks, such as cable networks, the Internet, wireless networks, cellular networks, satellite networks, other private and/or public networks, or any combination thereof. While the illustrated example represents the user device 104 accessing the service provider computers 1002 via the networks 1008, the described techniques may equally apply in instances where the user device 104 interacts with the service provider computers 1002 over a landline phone, via a kiosk, or in any other manner. It is also noted that the described techniques may apply in other client/server arrangements (e.g., set-top boxes, etc.), as well as in non-client/server arrangements (e.g., locally stored applications, peer to peer configurations, etc.).

As noted above, the user device 104 may be any type of computing device such as, but not limited to, a mobile phone, a smartphone, a personal digital assistant (PDA), a laptop computer, a desktop computer, a thin-client device, a tablet computer, a wearable device, or the like. In some examples, the user device 104 may be in communication with the service provider computers 1002 via the network 1008, or via other network connections.

In one illustrative configuration, the user device 104 may include at least one memory 1014 and one or more processing units (or processor(s)) 1016. The processor(s) 1016 may be implemented as appropriate in hardware, computer-executable instructions, firmware, or combinations thereof. Computer-executable instruction or firmware implementations of the processor(s) 1016 may include computer-executable or machine-executable instructions written in any suitable programming language to perform the various functions described. The user device 104 may also include geo-location devices (e.g., a global positioning system (GPS) device or the like) for providing and/or recording geographic location information associated with the user device 104.

The memory 1014 may store program instructions that are loadable and executable on the processor(s) 1016, as well as data generated during the execution of these programs. Depending on the configuration and type of the user device 104, the memory 1014 may be volatile (such as random access memory (RAM)) and/or non-volatile (such as read-only memory (ROM), flash memory, etc.). The user device 104 may also include additional removable storage and/or non-removable storage 1026 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 1014 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 1014 and the additional storage 1026, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 1014 and the additional storage 1026 are both examples of non-transitory computer storage media. Additional types of computer storage media that may be present in the user device 104 may include, but are not limited to, phase-change RAM (PRAM), SRAM, DRAM, RAM, ROM, Electrically Erasable Programmable Read-Only Memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 104. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The user device 104 may also contain communications connection(s) 1028 that allow the user device 104 to communicate with a data store, another computing device or server, user terminals, and/or other devices via the network 1008. The user device 104 may also include I/O device(s) 1030, such as a keyboard, a mouse, a pen, a voice input device, a touch input device, a display, speakers, a printer, etc.

Turning to the contents of the memory 1014 in more detail, the memory 1014 may include an operating system 1032 and/or one or more application programs or services for implementing the features disclosed herein such as a service engine 1003a. The service provider computer 1002 may also include a memory 1042 that includes a service engine 1003b. In this manner, the techniques described herein may be implemented by any one, or a combination of more than one, of the computing devices (e.g., the user device 104 or the service provider computer 1002). The service engine 1003 may be configured to implement the functions of the registration service 210, the provider service 209, the test harness 211, and any other function of a device or system described herein.

The service provider computers 1002 may also be any type of computing device such as, but not limited to, a mobile phone, a smartphone, a PDA, a laptop computer, a desktop computer, a thin-client device, a tablet computer, a wearable device, a server computer, a virtual machine instance, etc. In some examples, the service provider computers 1002 may be in communication with the user device 104 via the network 1008, or via other network connections.

In one illustrative configuration, the service provider computers 1002 may include at least one memory 1042 and one or more processing units (or processor(s)) 1044. The processor(s) 1044 may be implemented as appropriate in hardware, computer-executable instructions, firmware, or combinations thereof. Computer-executable instruction or firmware implementations of the processor(s) 1044 may include computer-executable or machine-executable instructions written in any suitable programming language to perform the various functions described.

The memory 1042 may store program instructions that are loadable and executable on the processor(s) 1044, as well as data generated during the execution of these programs. Depending on the configuration and type of service provider computer 1002, the memory 1042 may be volatile (such as RAM) and/or non-volatile (such as ROM, flash memory, etc.). The service provider computer 1002 may also include additional removable storage and/or non-removable storage 1046 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 1042 may include multiple different types of memory, such as SRAM, DRAM, or ROM. While the volatile memory described herein may be referred to as RAM, any volatile memory that would not maintain data stored therein once unplugged from a host and/or power would be appropriate. The memory 1042 and the additional storage 1046, both removable and non-removable, are both additional examples of non-transitory computer-readable storage media.

The service provider computer 1002 may also contain communications connection(s) 1048 that allow the service provider computer 1002 to communicate with a data store, another computing device or server, user terminals and/or other devices via the network 1008. The service provider computer 1002 may also include I/O device(s) 1050, such as a keyboard, a mouse, a pen, a voice input device, a touch input device, a display, speakers, a printer, etc.

Turning to the contents of the memory 1042 in more detail, the memory 1042 may include an operating system 1052 and/or one or more application programs or services for implementing the features disclosed herein including the service engine 1003b.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

The various examples further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most examples utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In examples utilizing a network server, the network server can run any of a variety of server or mid-tier applications, including HTTP servers, FTP servers, CGI servers, data servers, Java servers, and business application servers. The server(s) may also be capable of executing programs or scripts in response to requests from user devices, such as by executing one or more applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of examples, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or browser. It should be appreciated that alternate examples may have numerous variations from that described above. For example, customized hardware might also be used and/or particular elements might be implemented in hardware, software (including portable software, such as applets) or both. Further, connection to other computing devices such as network input/output devices may be employed.

Non-transitory storage media and computer-readable media for containing code, or portions of code, can include any appropriate media known or used in the art, including storage media, such as, but not limited to, volatile and non-volatile, removable and non-removable media implemented in any method or technology for storage of information such as computer-readable instructions, data structures, program modules, or other data, including RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by a system device. Based at least in part on the disclosure and teachings provided herein, a person of ordinary skill in the art will appreciate other ways and/or methods to implement the various examples.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

As described above, one aspect of the present technology is the gathering and use of data available from various sources to provide a comprehensive and complete window to a user's personal health record. The present disclosure contemplates that in some instances, this gathered data may include personally identifiable information (PII) data that uniquely identifies or can be used to contact or locate a specific person. Such personal information data can include demographic data, location-based data, telephone numbers, email addresses, Twitter ID's, home addresses, data or records relating to a user's health or level of fitness (e.g., vital sign measurements, medication information, exercise information), date of birth, or any other identifying or personal or health information.

The present disclosure recognizes that the use of such personal information data, in the present technology, can be used to the benefit of users. For example, the personal information data can be used to provide enhancements to a user's personal health record. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services or other services relating to health record management, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

What is claimed is:

1. A computer-implemented method, comprising:
   receiving configuration information associated with a patient record gateway, wherein the patient record gateway is associated with one or more patient record servers configured for storing electronic health records for a plurality of patients;
   defining, based at least in part on the configuration information, a schema configured to enable user devices to retrieve, via the patient record gateway, electronic health records from the one or more patient record servers;
   receiving, from a first user device, a request for connection information for connecting to the one or more patient record servers; and
   sending the schema to the first user device to enable the first user device to establish a connection with the one or more patient record servers.

2. The method of claim 1, wherein the configuration information includes a gateway conformance statement.

3. The method of claim 2, wherein defining the schema comprises defining the schema based at least in part on parsing the gateway conformance statement.

4. The method of claim 1, wherein the schema includes application programming interface (API) information defining a set of function calls for communication between the patient record gateway and the user devices.

5. The method of claim 1, wherein the schema is further configured to enable the first user device to download, via the connection with the one or more patient record servers, electronic health records as long as the configuration information associated with the patient record gateway is not updated.

6. The method of claim 5, further comprising:
   generating an updated schema based on updated configuration information associated with the patient record gateway;
   receiving, from the first user device, an update request for the updated schema; and
   sending the updated schema to the first user device to enable the first user device to establish a new connection with the one or more patient record servers.

7. The method of claim 1, wherein receiving the configuration information comprises receiving the configuration information from a second user device associated with an electronic health record system, wherein the one or more patient record servers and the patient record gateway are associated with the electronic health record system.

8. The method of claim 1, wherein the schema defines a protocol for authorization of the first user device to retrieve at least a portion of electronic health records of a patient associated with the first user device.

9. The method of claim 1, further comprising adding the patient record gateway to a list of supported patient record gateways configured to be accessible by the first user device.

10. The method of claim 1, wherein the configuration information is indicative that the patient record gateway passed a configuration test.

11. The method of claim 10, wherein the configuration test is a test of one or more capabilities of the patient record gateway using a gateway conformance statement and a set of test patient credentials.

12. The method of claim 11, wherein the configuration test comprises instructing a test harness to perform the configuration test by simulating authorization of a test patient using the set of test patient credentials and simulating retrieval of a test electronic health record associated with the set of test patient credentials.

13. A system, comprising:
   a memory configured to store computer-executable instructions; and
   a processor configured to access the memory and execute the computer-executable instructions to at least:
      receive configuration information associated with a patient record gateway, wherein the patient record gateway is associated with one or more patient record servers configured for storing electronic health records for a plurality of patients;
      define, based at least in part on the configuration information, a schema configured to enable user devices to retrieve, via the patient record gateway, electronic health records from the one or more patient record servers;
      receive, from a first user device, a request for connection information for connecting to the one or more patient record servers; and
      send the schema to the first user device to enable the first user device to establish a connection with the one or more patient record servers.

14. The system of claim 13, wherein the schema is further configured to enable the first user device to download, via the connection with the one or more patient record servers, electronic health records as long as the configuration information associated with the patient record gateway is not updated.

15. The system of claim 14, wherein the processor is further configured to access the memory and execute the computer-executable instructions to at least:
   generate an updated schema based on updated configuration information associated with the patient record gateway;
   receive, from the first user device, an update request for the updated schema; and
   send the updated schema to the first user device to enable the first user device to establish a new connection with the one or more patient record servers.

16. The system of claim 13, wherein receiving the configuration information comprises receiving the configuration information from a second user device associated with an electronic health record system, wherein the one or more patient record servers and the patient record gateway are associated with the electronic health record system.

17. One or more non-transitory computer-readable media comprising computer-executable instructions that, when executed by one or more processors of a computer system, cause the computer system to perform operations, comprising:
   receiving configuration information associated with a patient record gateway, wherein the patient record gateway is associated with one or more patient record servers configured for storing electronic health records for a plurality of patients;
   defining, based at least in part on the configuration information, a schema configured to enable user devices to retrieve, via the patient record gateway, electronic health records from the one or more patient record servers;
   receiving, from a first user device, a request for connection information for connecting to the one or more patient record servers; and
   sending the schema to the first user device to enable the first user device to establish a connection with the one or more patient record servers.

18. The one or more non-transitory computer-readable media of claim 17, wherein the schema defines a protocol for authorization of a patient to retrieve at least a portion of an electronic health record of the patient hosted by the one or more patient record servers.

19. The one or more non-transitory computer-readable media of claim 17, wherein the computer-executable instructions cause the computer system to perform further operations comprising adding the patient record gateway to a list of supported patient record gateways configured to be accessible by the first user device.

20. The one or more non-transitory computer-readable media of claim 17, wherein the configuration information is indicative that the patient record gateway passed a configuration test.

* * * * *